(12) United States Patent
Stefancik et al.

(10) Patent No.: US 6,549,798 B2
(45) Date of Patent: Apr. 15, 2003

(54) MAGNETIC RESONANCE ANGIOGRAPHY DATA

(75) Inventors: Robert M. Stefancik, Watertown, MA (US); Randy J. Earnest, Woburn, MA (US); Robert M. Weisskoff, Lexington, MA (US)

(73) Assignee: Epix Medical, Inc., Cambridge, MA (US)

(*) Notice: Subject to any disclaimer, the term of this patent is extended or adjusted under 35 U.S.C. 154(b) by 170 days.

(21) Appl. No.: 09/778,585

(22) Filed: Feb. 7, 2001

(65) Prior Publication Data

US 2002/0107443 A1 Aug. 8, 2002

(51) Int. Cl.[7] ............................................... A61B 5/055
(52) U.S. Cl. ...................... 600/419; 600/410; 324/307; 324/309
(58) Field of Search ................................ 600/419, 420, 600/422, 410, 411, 413, 509, 521; 324/307, 309

(56) References Cited

U.S. PATENT DOCUMENTS

| | | | |
|---|---|---|---|
| 5,297,551 A | 3/1994 | Margosian et al. | 128/653.2 |
| 5,364,614 A | 11/1994 | Platzek et al. | 424/9 |
| 5,417,213 A | 5/1995 | Prince | 128/653.3 |
| 5,647,360 A | 7/1997 | Bani-Hashemi et al. | 128/653.1 |
| 5,650,136 A | 7/1997 | Platzek et al. | 424/9.36 |
| 5,681,543 A | 10/1997 | Schmitt-Willich et al. | 424/934 |
| 5,695,739 A | 12/1997 | Schmitt-Willich et al. | 424/9.42 |
| 5,733,528 A | 3/1998 | Felder et al. | 424/9.365 |
| 5,792,056 A | 8/1998 | Prince | 600/420 |
| 5,798,092 A | 8/1998 | Schmitt-Willich et al. | 429/9.364 |
| 5,799,649 A | 9/1998 | Prince | 128/653.4 |
| 5,812,691 A | 9/1998 | Udupa | 382/128 |
| 5,820,849 A | 10/1998 | Schmitt-Willich et al. | 424/9.36 |
| 5,848,121 A | 12/1998 | Gupta et al. | 378/62 |
| 5,876,698 A | 3/1999 | Schmitt-Willich et al. | 424/9.363 |
| 5,888,576 A | 3/1999 | Nagano | 426/643 |

(List continued on next page.)

FOREIGN PATENT DOCUMENTS

| | | | |
|---|---|---|---|
| JP | 2000-175885 | * 6/2000 | ........... A61B/5/055 |
| WO | WO 9532741 | 12/1995 | |
| WO | WO 9609840 | 4/1996 | |
| WO | WO 96/23526 | 8/1996 | |
| WO | WO 9725073 | 7/1997 | |
| WO | WO 9805625 | 2/1998 | |
| WO | WO 9805626 | 2/1998 | |
| WO | WO 9838738 | 9/1998 | |
| WO | WO 0030688 | 6/2000 | |

OTHER PUBLICATIONS

"Magnetic Resonance Imaging Clinics of North America Body MR Angiography" edited by S.A. Mirowitz and G. Krinsky, 6 (2) © May 1998 W.B. Saunders Co.

"Clinical Magnetic Resonance Imaging" edited by R.R. Edelman, M.B. Zlatkin, and J.R. Hesselink, © Jan. 1996 W.B. Saunders Co.

*Primary Examiner*—Hieu T. Vo
(74) *Attorney, Agent, or Firm*—Fish & Richardson, P.C., P.A.

(57) ABSTRACT

A method is provided for improved visualization of vascular structures contained within magnetic resonance angiograms, particularly steady-state contrast-enhanced magnetic resonance angiograms. The disclosed methods include manipulating the relative enhancement levels of the arterial and venous blood pools images with respect to each other and to the surrounding anatomy. This manipulation is meant to optimize visualization of one or both of the individual blood pools without the necessity of completely obscuring or removing the supporting information given by presentation of the other blood pool and/or the surrounding anatomy.

22 Claims, 4 Drawing Sheets

U.S. PATENT DOCUMENTS

| | | | |
|---|---|---|---|
| 5,924,987 A | 7/1999 | Meaney | 600/420 |
| 5,928,148 A | 7/1999 | Wang et al. | 600/420 |
| 6,043,655 A | 3/2000 | Makita et al. | 324/309 |
| 6,073,042 A | 6/2000 | Simonetti | 600/420 |
| 6,075,836 A | 6/2000 | Ning | 378/98.12 |
| 6,192,264 B1 * | 2/2001 | Foo et al. | 600/413 |
| 6,198,959 B1 | 3/2001 | Wang | 600/413 |
| 6,246,897 B1 * | 6/2001 | Foo et al. | 324/307 |
| 2002/0087070 A1 * | 7/2002 | Foo et al. | 600/420 |

* cited by examiner

MAGNETIC RESONANCE ANGIOGRAPHY DATA

FIELD OF THE INVENTION

The application relates generally to the use of magnetic resonance imaging (MRI) data. More specifically, the application relates to the improved visualization of steady-state contrast-enhanced MRI anatomical data with superimposed physiologic data. Most specifically, the application relates to improving the visualization of the arterial and venous blood pools in magnetic resonance angiography (MRA).

BACKGROUND OF THE INVENTION

Cardiovascular disease is a primary health threat. Therefore, it is essential to detect cardiovascular disease in its early stages. One manner to detect cardiovascular disease is through the use of magnetic resonance angiography (MRA). The primary goal of MRA is to non-invasively acquire necessary clinical information via image data to diagnose and plan treatment for various cardiovascular problems. Unlike the current standard of treatment, X-ray angiography, MRA does not require insertion of a catheter for introduction of the contrast agent. Additionally, X-ray angiography (XRA) contrast agents are nephrotoxic, whereas MRA contrast agents are typically much better tolerated by the body. Although MRA is only beginning to emerge into mainstream clinical practice, it has the potential to become the primary modality to image cardiovascular tissues in the future.

In MRA, the first generation of contrast agents introduced into the clinical market were known as ECF agents. These agents rapidly leave the bloodstream and 'leak' into the fluids in the body, reducing contrast between the blood pool and the rest of the body quickly. Intravascular agents, through a variety of mechanisms, extend the persistence of the contrast agent in the blood pool, allowing for longer image acquisition periods. Until intravascular agents were introduced, MRA image acquisition was typically limited to the first pass of the contrast bolus, much like XRA, due to the extensive leakage of the contrast agent into the extracellular fluid. Intravascular agents remain in the blood pool much longer, allowing for longer MR scan times, greater potential resolution, and less reliance on timing of the introduction of the contrast bolus, etc. This longer persistance in the blood, however, introduces a problem in visualization. Because of simultaneous enhancement of both the arterial and venous blood pools, the vessels obscure each other when using projection methods (such as maximum intensity projection (MIP)), and can potentially confuse the reader even when viewing the source data.

Prior methods for manipulating the visualization of MRA data include segmentation methodologies and Digital Subtraction Angiography (DSA). Each of these methods, however, disadvantageously remove a significant amount of potentially useful information and/or have reliability issues. Additionally, reliance on capturing a contrast bolus delivery (for DSA) can be difficult, or almost impossible (as in carotid imaging). Additionally, DSA has been presented in the past as a method of removing background information, not as a technique for removal or reduction of other vascular structures. These vascular structures, however, also contain potentially relevant diagnostic information. Computer segmentation methods alone allow for the loss of supporting information, such as anatomic landmarks from surrounding anatomy, and exclusion of potentially clinically significant information.

Previous work in the area of angiographic image processing tends to relate to the removal of background information to enhance vessel visibility without removing the high intensity signal that represents the blood pool. U.S. Pat. No. 5,297,551 discloses a method of intensity manipulation. However, a method such as this does not effectively differentiate between the arterial and venous blood pools, which in this case is very desirable.

This task of differentiating between the arterial and venous blood pools is effectively independent of enhancing visibility by manipulating the background regions. Because no contrast agents until the present time would remain in the blood long enough to effectively enhance both blood pools at the same level simultaneously, no previous work is known to have been done to effectively overcome this effect.

U.S. Pat. No. 6,073,042 to Simonetti shows a method of displaying three-dimensional MRA images in which arteries can be distinguished from veins. The Simonetti method, however, requires acquiring multiple image series as a function of time and requires many calculations to find curves that simulate the change of voxel intensity as a function of time. As is the case with most MRA methods, image sets are closely temporally spaced (i.e. short TR) in order to accurately represent dynamic phenomena. Unfortunately, this necessarily limits the resolution of the resultant images compared with images required over longer time periods. There remains a need for MRI techniques that faithfully convey physiological phenomena in images with high spatial resolution. In the case of MRA, there remains a need for techniques which present high resolution images of the vasculature and indicate whether those vessels are arteries or veins.

SUMMARY OF THE INVENTION

The invention provides a method of visualizing MRI data taken from two data sets, one set that can comprising high spatial resolution anatomical image data, and the other that can comprise physiological data which is not necessarily of as high a resolution as the other data set. The method then combines the two data sets to produce a clinically useful MR image. The methods disclosed herein are especially useful for improving the visualization of contrast enhanced arterial and venous blood pools in magnetic resonance angiography (MRA). In general, these methods allows for the rapid generation of clinically useful MRA images which appear to have a high spatial resolution and detailed anatomical information while also illustrating arterial-venous differentiation.

In a preferred embodiment, the invention provides methods for improving visualization of contrast enhanced MRA data in which simultaneous enhancement of the artery and vein portions of the circulatory system is present (i.e. the "steady state"). The invention mathematically manipulates the relative enhancement of the arterial and venous blood pools to allow differentiation between the two pools without removing either pool from the images. This allows the viewer considerable information retention in the data while also allowing for rapid recognition of the anatomy of interest. This method of problem solving exploits the novel strengths of intravascular contrast in the steady state while removing the difficulty of producing rapid visualization of these data sets.

In accordance with one embodiment of the invention, the method of improving the visualization of magnetic resonance angiography data taken from a patient, generally includes:

providing a display device;

acquiring a first set of data representing a steady state contrast enhancement of an arterial blood pool and a venous blood pool of the patient;

acquiring a single second set of data that, in combination with the first set of data, provides information sufficient to differentiate between the arterial blood pool and the venous blood pool of the patient;

combining intensities in predetermined locations by a predetermined amount of the first and the second sets of data to produce a third set of data representing the arterial and the venous blood pools in comparable resolution with each other; and displaying the third set of data upon the display device.

DETAILED DESCRIPTION OF THE INVENTION

The invention provides methods which improve visualization of MRI data, especially MRA data in which the arterial and venous blood pools are similarly enhanced. The methods are especially useful for improving the visualization of contrast enhanced arterial and venous blood pools in magnetic resonance angiography (MRA). In general, the methods provide for the rapid generation of clinically useful MRA images that appear to have a high spatial resolution and detailed anatomical information while also illustrating arterial-venous differentiation.

To obtain improved visualization of MRA data according to the invention, it is necessary to acquire two sets of data. The first data set is a high resolution, steady state MRA data set acquired by standard methods known to those skilled in the art. "Steady state" shall mean herein the time after contrast agent administration during which the arterial and venous blood pools are not substantially differentiable by their respective signal intensities. The time period during which the steady state exists is dependent on the person's physiology, the contrast agent employed, and the anatomical area being imaged. The first data set is preferably at least of equivalent spatial resolution, and is preferably the highest resolution available.

The second data set can be another MRI sequence (MRA or otherwise), or a derivative data set created by computer post-processing algorithms that are specifically designed to provide the information necessary to differentiate between the arterial and venous blood pools. The second data set should comprise at least some of the same anatomic area as the first data set, and it should be able to be at least partially registered to the first data set. Furthermore, the second data set should contain some information that distinguishes venous from arterial blood. Any MR image sequence that exploits differential characteristics of the arterial and venous blood pools (oxygenation levels, flow direction, flow velocity, etc.) can be used in this manner as the second data set. Examples of suitable second data sets include, inter alia, phase contrast (PC), time of flight (TOF), and BOLD images. (These and other MR imaging techniques are thoroughly described in "Magnetic Resonance Imaging Clinics of North America: Body MR Angiography" edited by S. A. Mirowitz and G. Krinsky, 6(2), © May 1998 W. B. Saunders Co., which is hereby incorporated by reference, and the references cited therein.) The second data set may alternatively be derived from the first data set by a post-processing method such as those known in the art, including intensity thresholding, intensity thresholding with connectivity constraints (such as arteriovenous separation specific algorithms, "fuzzy connectivity", phase information utilization, and others). (A comprehensive discussion of various imaging techniques may be found in the textbook "Clinical Magnetic Resonance Imaging" edited by R. R. Edelman, M. B. Zlatkin, and J. R. Hesselink, © January 1996 W. B. Saunders Co., which is hereby incorporated by reference,).

Figure 4:
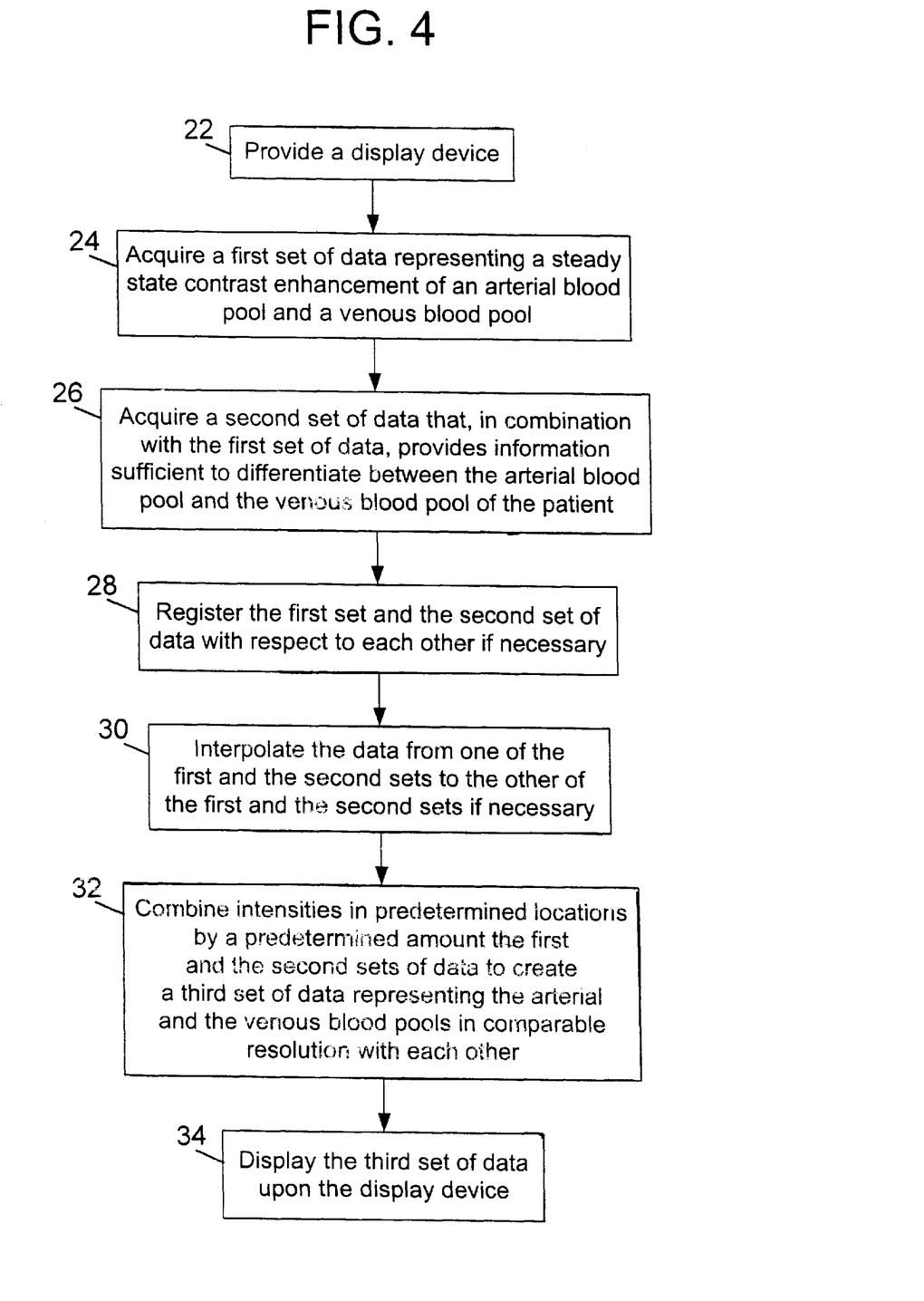
FIG. 4 is a flowchart of an exemplary method for obtaining a contrast enhanced MRA data set in accordance with the invention.

In accordance with embodiments of the invention, a method of improving the visualization of magnetic resonance angiography data taken from a patient is illustrated in FIG. 4. At stage 22, a means for displaying images is provided. For example, a MRI scanner and computer system capable of generating two-dimensional representations of three dimensional data, examples of which are well known to those skilled in the art, and include principally maximum intensity projection (MIP) and volume rendering (VR) means. MRI equipment may be acquired from General Electric, Siemens, Philips, Marconi and others, and typical workstations include General Electric's Advantage Windows, Siemens' 3D Virtuoso and Syngo, Philips' EasyVision, Vital Images' Vitrea, and Algotec's ProVision. A preferred programming language for implementing the method is IDL (Interactive Data Language, Research Systems), but in principle any language compatible with the hardware system may be appropriate.

Figure 2:
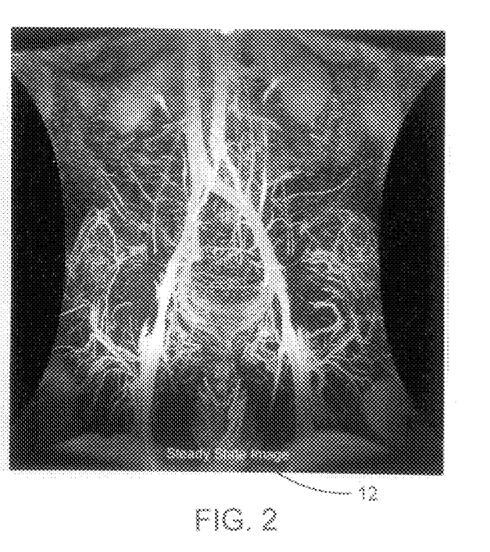
FIG. 2 is a steady state magnetic resonance angiography image.

At stage 24, a first set of data representing a steady state contrast enhancement of an arterial blood pool and a venous blood pool of the patient is provided. The first set of data can be acquired at a time delayed from an introduction of a MRI contrast agent to the patient such that the contrast enhancement of the data is roughly equivalent in both the arterial and venous blood pools (i.e. at the "steady state"). An example of a high resolution steady state MRA imaging is shown in FIG. 2, which shows simultaneous and substantially equivalent enhancement of the arterial and venous blood pools that complicates rapid clinical analysis of the image.

In principle, any MRI contrast agent may be suitable, including those which are currently commercially available, e.g. Magnevist™ (Shering AG), ProHance™ (Bracco SpA), and Ferridex™ (Advanced Magnetics, Inc.). Preferred are contrast agents comprising gadolinium(III), see "Gadolinium(III) Chelates as MRI Contrast Agents: Structure, Dynamics, and Applications" by P. Caravan et al. Chem. Rev. 99, 2293–2352 (1999), incorporated herein in its entirety by reference. Developmental contrast agents that may be used include Eovist™ (Schering AG) and the contrast agents disclosed in U.S. Pat. Nos. 5,798,092 and 5,695,739; and MultiHance™ (Bracco SpA) and the contrast agents disclosed in U.S. Pat. No. 5,733,528. Particularly preferred are "blood pool" MRI contrast agents, see "Blood pool Contrast Agents for Cardiovascular MR Imaging" by L. J. M. Kroft et al. JMRI 10, 395–403 (1999), incorporated herein by reference, and "The Future of Contrast-Enhanced Magnetic Resonance Angiography: Are Blood Pool Agents Needed?" by A. Mühler Invest. Radiol. 33, 709–714 (1998), also incorporated herein by reference. Examples of blood pool contrast agents include MP-2269 (Mallinckrodt, Inc.) and the contrast agents disclosed in U.S. Pat. No. 5,888,576; MS-325 (EPIX Medical, Inc.) and the contrast agents disclosed in PCT publication WO 96/23526, incorporated herein by reference; P760 (Geurbet); Gadomer-17™ (Schering AG) and the contrast agents disclosed in U.S. Pat. Nos. 5,876,698, 5,820,849, 5,681,543, 5,650,136, and 5,364,614; Clariscan™ (Nycomed Amersham) and the contrast agents disclosed in PCT publications WO 96/09840 and WO 9725073; and B22956/1 (Bracco SpA) and the contrast agents disclosed in PCT publications WO 00/30688, WO 98/05625, WO 98/05626, WO 95/32741, WO 98/38738, WO 95/32741, and U.S. Pat. No. 5,649,537.

Figure 1:
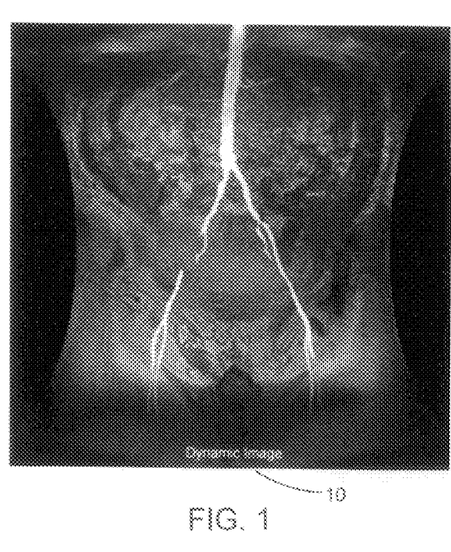
FIG. 1 is a dynamic magnetic resonance angiography image.

At stage 26, a single second set of data is acquired that, in combination with the first set of data, provides information sufficient to differentiate between the arterial blood pool and the venous blood pool of the patient. For example, information sufficient to differentiate between the arterial blood pool and the venous blood pool of the patient includes differences in phase, concentration of contrast agent, etc. An example of a dynamic MRA image is shown in FIG. 1, in which the arterial blood pool is clearly enhanced and differentiable via intensity with respect to the unenhanced venous blood pool. This data set may be a second acquired MRI data set or a postprocessing-generated set as described above. It may not necessary that the first and second sets of data be obtained in a specified order. In some cases, it may be preferable to acquire the data set comprising "physiological data" first, and the higher resolution "anatomical data set" thereafter. In a typical embodiment, the second data set is a dynamic MRA acquired during and/or shortly after (approximately 5 min) intravenous contrast agent administration (see Prince U.S. Pat. No. 5,417,213), and the first data set is a conventional steady state scan.

At stage 28, the first set and the second set of data are registered with respect to each other if necessary. This may not need to be done in some cases, such as when the two data sets are explicitly registered. However, once the two data sets are obtained, spatial registration of the two data sets may be necessary. The specific method of registration of the two data sets is dependent on the method of generating the second data set. Specific algorithms to perform this registration are well documented in the literature and known to those skilled in the art. In the case of post-processed data, the registration is unnecessary because the data is calculated from the target data itself, and thus the second data set is inherently registered. In the case of sequential MR acquisitions, a simple transform using the information contained in a standard DICOM header may suffice. In other cases, registration using a commercially available package may be necessary to provide the desired accuracy.

At step 30, the data from one of the first and the second sets is interpolated to the other of the first and the second sets if necessary, such as when the data sets are of different spatial resolutions. In the case in which a lower resolution dynamic data set is to be used in conjunction with a higher resolution steady state data set, it is preferable to interpolate the lower resolution data set to the spatial resolution of the higher resolution data set. In cases where this interpolation is necessary, any generally accepted algorithm for interpolation can be used as is known to those skilled in the art.

At stage 32, the intensities of the first and the second sets of data are combined in predetermined locations by a predetermined amount to produce a third set of data that represents the arterial and the venous blood pools in comparable resolution with each other. The third data set having contrast enhanced MRA data is a result of the direct calculation of modified image intensities resulting from the combination of individual values from the data elements from the first and second data sets. As noted above, it may have been necessary to register and interpolate the data elements of the first and the second data sets. Some of the algorithms that can be used to generate this new data set are described below.

At stage 34, the third data set is displayed on the display device. The contrast enhanced MRA data may be displayed on a system or workstation capable of processing and displaying the data sets. This system can be a standard visualization workstation as are currently used in typical clinical environments. The increased contrast enhancement of the arterial portion of the data set will significantly improve the visualization of the arterial structures in the data set, especially when using a projection method of visualization of the data set. Specifically, should the intensity levels of either blood pool be enhanced such that every element in the selected blood pool has an intensity that exceeds that of the other blood pool and surrounding tissues, visualization methods such as maximum intensity projection (MIP) and volume rendering (VR) can unambiguously indicate that blood pool distinctly from the rest of the data. Furthermore, if the unenhanced blood pool's contrast level is differentiable from the surrounding tissues, these three regions (the enhanced blood pool, the unchanged blood pool, and the surrounding tissue) can be manipulated by the workstation software due to their intensity levels to selectively show any or all combinations of the three regions that are preferred for optimal visualization of the data set.

Creating the Output Data Set

Definitions of symbols used herein:
- S=A steady state data set, i.e. the first data set comprising "anatomical" information;
- D=A second data set, another MRI scan comprising information which differentiates the arterial and venous blood pools;
- $D_1$=A second data set which is derived from the first data set by a postprocessing method comprising information which differentiates the arterial and venous blood pools;
- O=An output data set;
- $\alpha,\beta,\gamma$=Scaling factors for the data sets which are combined to generate the output data set O;
- a=A subset of S consisting of the arterial blood pool signal. This subset can be directly determined by any desired postprocessing algorithm;
- v=A subset of S consisting of the venous blood pool signal, generated by a similar method as a;
- b=The combined arterial and venous blood pool sets, i.e. the vasculature; and
- t=S−b, subset of S consisting of non-blood tissues.

Each of the sets a, b, v, t, S, D, $D_1$, and O have the same dimensions, i.e. they have been interpolated and registered as described above if necessary.

When both the first and second data sets are obtained from independent MRI scans, an output data set O is then produced according to any of the following equations:

$$O=\alpha S\pm\beta D \qquad (I)$$

$$O_i=\min(\alpha S_i,\beta D_i) \qquad (II)$$

In these equations, $\alpha$ and $\beta$ are predetermined relative weighting factors. In equation I the output data set O is generated by ordinary set arithmetic. In Equation II, the output set O is preferably generated by taking only the value at each coordinate in space with the lowest $T_1$, i.e. the "minimum" signal.

In equation I, the values $\alpha$ and $\beta$ are preferably not equal to each other, and are preferably in the range $1>\alpha,\beta\geqq 0$ and preferably $\alpha+\beta=1$. Most preferably, for arterial enhancement the values are approximately $\alpha=0.75$ and $\beta=0.25$, in which case the arterial blood pool appears to be brighter than the venous blood pool thereby increasing clinical utility. If arterial enhancement is desired to be greater than venous enhancement, then $\alpha$ should be greater than $\beta$ when using the addition operator, and vice versa when using the subtraction operator. Using weighting factors that add to unity will generally help to ensure that O will be of similar intensity magnitude to the input data sets. In equation II, the values $\alpha$ and $\beta$ are preferably both equal to unity in which case the resultant data set O has an almost complete suppression of the venous blood pool signal and the arterial blood pool appears to be presented at the high resolution at which the steady state scan was acquired.

When one of the first and second data sets is derived from the other data set by a postprocessing algorithm, an output data set O is then produced according to any of the following equations:

$$O=\alpha S\pm\beta D_1 \qquad (III)$$

$$O=\alpha a\pm\beta v\pm\gamma t \qquad (IV)$$

Similar to the case above, in these equations, $\alpha,\beta$, and $\gamma$ are predetermined relative weighting factors. The values $\alpha$ and $\beta$ should not equal to each other. Preferred values are in the range $1>\alpha,\beta,\gamma\geqq 0$ and preferably $\alpha+\beta+\gamma=1$. Most preferably, for arterial enhancement the values are approximately $\alpha=0.6,\beta=0.2$, and $\gamma=0.2$. If arterial enhancement is desired to be greater than venous enhancement, then $\alpha$ should be greater than $\beta$ and $\gamma$ when using the addition operator, and vice versa when using the subtraction operator. Note that addition and subtraction are not necessarily equivalent operators when using mirrored weights, due to the relevance of the background tissue. Using weighting factors that add to unity will help to ensure that O (output data set) will be of similar intensity magnitude to the input data sets.

Figure 5:
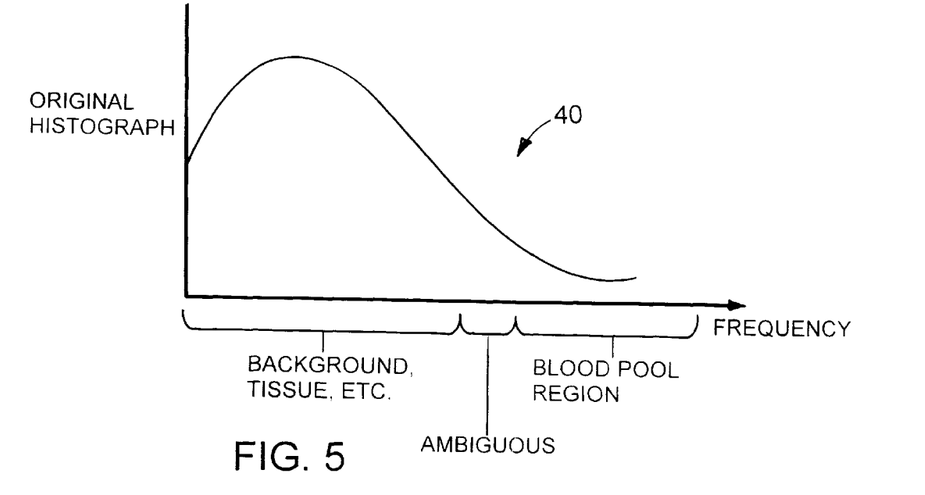
FIG. 5 is a histogram before the effects of intensity manipulations.
Figure 6:
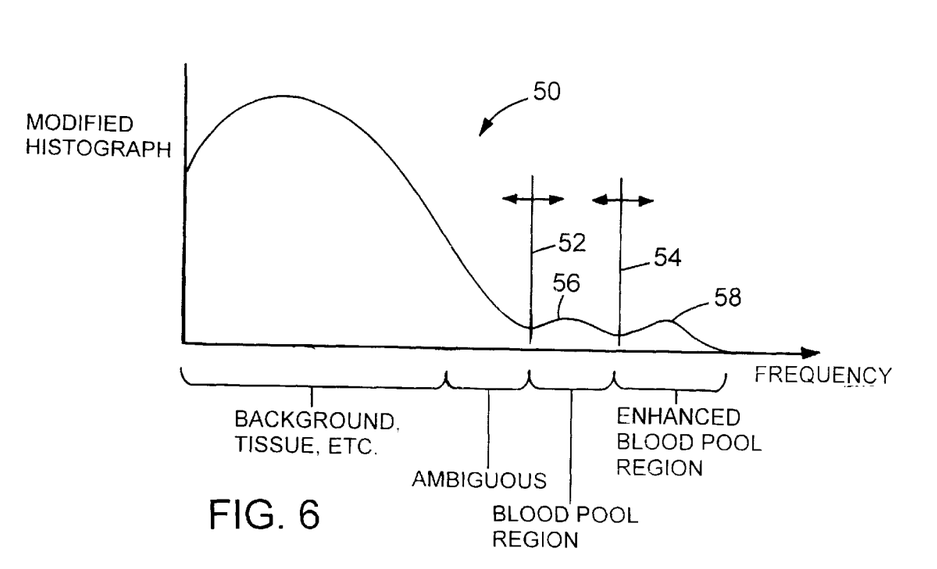
FIG. 6 is a histogram that shows the effects of intensity manipulations.

FIGS. 5 and 6 are exemplary histograms substantially representative of an MRA data set before and after contrast enhancement, respectively. These histograms are graphs which represent the number of occurrences of a specific grayscale value in an image. The x axis typically represents the intensity, while the y axis represents the frequency of a specific value. The utility of a histogram in this case is to determine if a portion of the image is differentiable by intensity values alone. This would be visible in the histogram by two or more separable intensity groupings along the x-axis. FIG. 5 is representative of the histogram 40 (a graph representing the occurrences of individual brightness values in the image) for a steady state data set. This graph is for illustration purposes only, and does not represent the actual appearance of an image histogram. On the x-axis there are labels that roughly correspond to the physical structures' intensity distributions. In FIG. 5, we can see that the background and tissue occupy a lower average intensity than the blood pool, and that there is likely some overlap caused by various factors (partial volume effect being a primary example). However, the primary importance is to note is that because the artery and vein occupy the same intensity distribution in the original image, it is not possible to separate them by their intensity values alone. Most common visualization methods such as MIP and VR depend on intensity differences to control what is displayed to the user, thus using these methods it isn't preferable in this case to differentially visualize either blood pool alone. FIG. 6 represents the image histogram after the methods of contrast enhancement manipulation disclosed herein have been performed. The advantage is exemplified by noting that regions 56 and 58 are now separable via their intensity distributions due to the processing. This allows the MIP and VR algorithms to differentially display the two blood pools using these standard algorithms as commonly implemented.

FIG. 5 shows a histogram 40 of an MRA before the effects of intensity manipulations. The background tissue takes up most of the histogram. A small region in the center is ambiguous due to partial volume effects from small vessels, noise and fat enhancements. The blood pool region, which comprise the arterial and the venous blood pools, is on the right side of the histogram. Because the arterial and the venous blood pools reside on the same portion of the histogram, it is difficult to see both blood pools at once.

FIG. 6 shows an exemplary modified histogram 50 of an MRA that shows the effects of intensity manipulations. Because the intensity of one of the blood pools has been increased, that blood pool can be seen at point 58. The blood pool that did not have its intensity modified can be seen at point 56. The separations of regions at 52 and 54 can be adjusted such that the regions 56 and 58 can each have their individual intensity manipulated to create desired visualizations. By doing the outlined intensity manipulation, one can now use pre-existing workstations and their software routines to selectively view the different blood pools, which typically isn't possible with the current generation of ECF contrast agents, nor is it typically possible using intravascular agents without manipulating the relative intensities of the blood pools. However, by doing this manipulation one is able to make a more optimal visualizaton result directly from the data using the commonly accepted techniques of MIP and VR visualizations of the MRA volumes. This ability enables the viewer to rapidly visualize the vessels of interest and locate potential abnormalities for further study in the planar image sets, as well as rapidly determining those patients in which normal blood flow is present.

Additionally, the images generated by the invention have an esthetic appeal since they appear to be conventional MRI images which are readily appreciated by a clinician, and the arterial and venous blood pools are clearly differentiated.

EXAMPLE

An adult human subject was administered MS-325 by intravenous injection and a series of dynamic MRA scans were collected of the thorax during the first pass of contrast agent with the following imaging parameters:

Instrument: 1.5 T GE Medical Systems
Pulse sequence: T1-weighted SPGR, TE=1.8, TR=8.7, flip angle=40
Resolution: 1.8×1.8×3.6 mm
Dimensions: 512×192×52
Field of View: 440×330 mm An MIP of this data set is presented in FIG. 1. During the steady state the patient was imaged again to generate a second data set with the following modifications to the above parameters:

Pulse sequence: T1-weighted SPGR, TE=2.1, TR=18.7, flip angle=30
Resolution: 0.9×0.9×1.8 mm
Dimensions: 512×512×128

Figure 3A:
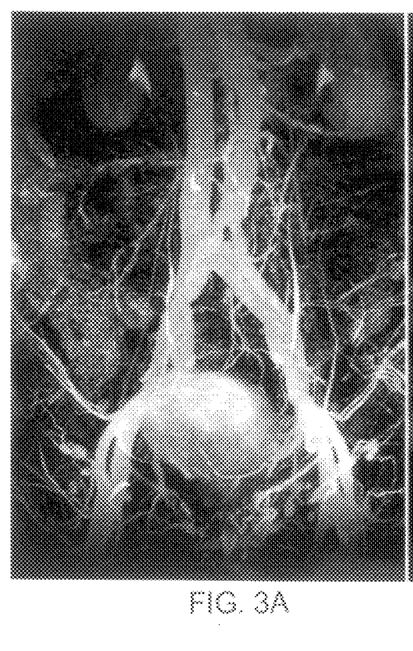
FIGS. 3a and 3b are exemplary images of a data set before and after processing.
Figure 3B:
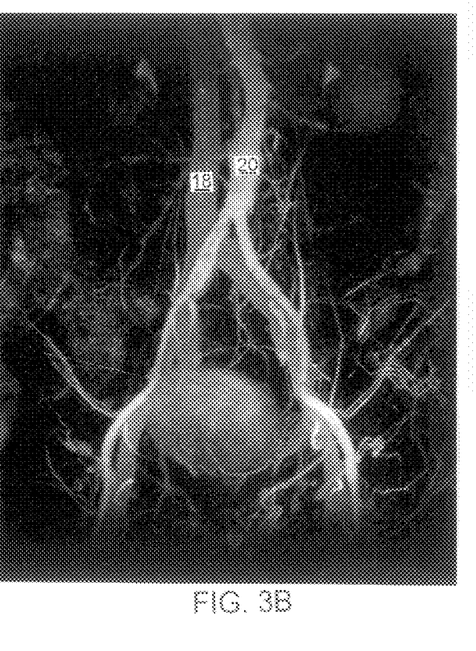

An MIP of this data set is presented in FIG. 2. The data set from the dynamic scan was interpolated up to the resolution of the steady state scan and the two were combined according to equation I (vide supra), with $\alpha=0.75$ and $\beta=0.25$, by the computer program which is attached as an Appendix hereto. The output set (FIG. 3b) clearly illustrates the difference between the aorta and the vena cava.

It should be understood that the foregoing is illustrative and not limiting and that modifications may be made by those skilled in the art without departing from the spirit of the invention. Accordingly, reference should be made primarily to the accompanying claims, rather than the foregoing specification, to determine the scope of the invention.

Appendix – Computer Program Listing

```
;
;      Arterial enhancement example
;      Company: EPIX Medical, Inc. Cambridge MA
;      Date: December, 1999

PRO ArterialEnhance

;
;      READ IN DATA FROM THE DICOM HEADER
;

; Use Mac OS protocol to pick the file(s)
img_name = Dialog_Pickfile(Filter='*.dcm', /Read, /Multiple)
dyn_name = Dialog_Pickfile(Filter='*.dcm', /Read, /Multiple)

image_count = N_ELEMENTS(img_name)

; Create a DICOM object to hold the information from the files
dci = OBJ_NEW('IDLffDICOM')
; Create an array to hold the position variables
image_position = fltarr(3)
; Create a vector to hold the slice plane positions
slice_position=fltarr(image_count)

if(QUERY_DICOM(img_name[0], imginfo) EQ 1) THEN BEGIN res = dci->Read(img_name[0])
```

19

```
    val = dci->GetValue('0028'x,'0010'x, /no_copy) ; rows
    rows = Fix(*val[0])
    val = dci->GetValue('0028'x,'0011'x, /no_copy) ; columns
    cols = Fix(*val[0])
    val = dci->GetValue('0028'x,'0030'x, /no_copy) ; pixel size
    vsize = Str_Sep(*val[0], '\')
    vxs = Float(vsize[0])
    vys = Float(vsize[1])
    val = dci->GetValue('0018'x,'0050'x, /no_copy) ; slice
thickness
    vzs = Float(*val[0])
    val = dci->GetValue('0028'x,'0102'x, /no_copy) ; High Bit
    HB= Fix(*val[0])
    val = dci->GetValue('0028'x,'0100'x, /no_copy) ; Bits
Allocated
    BA = Fix(*val[0])
    val = dci->GetValue('0028'x,'0101'x, /no_copy) ; Bits
Stored
    BS= Fix(*val[0])

;
;    INITIALIZE VARIABLES
;

; Create the output image volume
    data_array=MAKE_ARRAY(rows,cols,image_count,TYPE=imginfo.pi
xel_type)
    temp_array=MAKE_ARRAY(rows,cols,image_count,TYPE=imginfo.pi
xel_type)

FOR j=0, image_count-1 DO BEGIN
        if(QUERY_DICOM(img_name[j], imginfo) EQ 1) THEN BEGIN
```

```
            res = dci->Read(img_name[j])
            img_orient = dci->GetValue('0020'x,'0032'x,/no_copy)
            img_orient = Str_Sep(*img_orient[0],'\')
            slice_position[j] = Float(img_orient[1])
            data_array[*,*,j]=READ_DICOM(img_name[j])

ENDIF
    ENDFOR

ENDIF

; Read in the dynamic data set
dyn_count = N_ELEMENTS(dyn_name)
dyn_slc_position = fltarr(dyn_count)

if(QUERY_DICOM(dyn_name[0], dimageinfo) EQ 1) THEN
dyn_array=MAKE_ARRAY(dimageinfo.dimensions[0],dimageinfo.dimensi
ons[1],dyn_count,TYPE=dimageinfo.pixel_type)

;
;       READ IMAGE DATA FROM FILES
;

FOR j=0, dyn_count-1 DO BEGIN
        if(QUERY_DICOM(dyn_name[j], dimageinfo) EQ 1) THEN
BEGIN
            res = dci->Read(dyn_name[j])
            dyn_array[*,*,j] = READ_DICOM(dyn_name[j])
            img_orient = dci-
>GetValue('0020'x,'0032'x,/no_copy)
            img_orient = Str_Sep(*img_orient[0],'\')
```

21

```
                    image_position[0] = Float(img_orient[0])
                    image_position[1] = Float(img_orient[1])
                    image_position[2] = Float(img_orient[2])
                    dyn_slc_position[j] = image_position[1]

ENDIF
        ENDFOR

OBJ_DESTROY, dci

;
    ;     INTERPOLATED VALUES INTO temp_array
    ;

coeff_array = fltarr(image_count,2)
        ref_array   = intarr(image_count,2)

FOR j=0, image_count-1 DO BEGIN
        p1 = slice_position[j]
        ref1= 0
        ref2 = 0 index = WHERE(dyn_slc_position LT p1, count_lessthan)
            IF ( count_lessthan GT 0) THEN BEGIN
                bm = MAX( dyn_slc_position[index])
                ref1 = WHERE( dyn_slc_position EQ bm)
            ENDIF index = WHERE( dyn_slc_position EQ p1, count_equalto )
        IF (count_equalto EQ 1) THEN BEGIN
            copyref = index
```

```
        ENDIF index = WHERE(dyn_slc_position GT p1,
count_greaterthan)
        IF( count_greaterthan GT 0 ) THEN BEGIN
            sm = MIN (dyn_slc_position[index])
            ref2 = WHERE( dyn_slc_position EQ sm)
        ENDIF setcopy = 0
        inbounds = 0 if (count_equalto EQ 1) THEN BEGIN
        setcopy = 1

ENDIF ELSE BEGIN
    if ((count_lessthan GT 0) AND (count_greaterthan GT 0))
THEN BEGIN
        inbounds = 1

ENDIF ELSE BEGIN

ENDELSE
    ENDELSE

IF (setcopy EQ 1) THEN BEGIN
        temp_array(*,*,j) = dyn_array(*,*,copyref)
    ENDIF ELSE BEGIN
        IF (inbounds EQ 1) THEN BEGIN d1 = abs(p1-bm)
        d2 = abs(p1-sm)
```

23

```
            norm = d1+d2
            d1 = d1/norm
            d2 = d2/norm
            temp_array(*,*,j) =
fix(d1*float(dyn_array(*,*,ref2))+d2*float(dyn_array(*,*,ref1)))
            ENDIF ELSE BEGIN
                temp_array(*,*,j) = 0
            ENDELSE
        ENDELSE

ENDFOR

; remove dynamic array dyn_array=0

;
;       SET alpha AND beta AND PRECALCULATE WEIGHTING VALUES
;       GENERATE OUTPUT SET "O" ACCORDING TO EQUATION I
;

alpha = 0.75
        beta = 0.25

FOR j=0, image_count-1 DO BEGIN
            data_array[*,*,j] =
fix(TEMPORARY(data_array[*,*,j])*alpha)
            temp_array[*,*,j] =
fix(TEMPORARY(temp_array[*,*,j])*beta)
        ENDFOR
```

```
    data_array = TEMPORARY(data_array) + temp_array

;
;   WRITE OUT (SAVE) THE DATA ARRAY TO SEQUENTIAL RAW FILES
;   FOR CONVERSION TO DICOM AND SUBSEQUENT DISPLAY

FOR j=0, image_count-1 DO BEGIN

; Specify Output folder
    outpath = 'HD:Desktop Folder:Raw Output'

; Generate output file name
    pathname = img_name[j]
    pathname = str_sep(pathname,':')
    filename = str_sep(pathname[(n_elements(pathname)-1)], '.')
    outfilename = filename[0] + '.raw'
    outfilename = outpath + ':' + outfilename
    print, outfilename get_lun, outlun
    openw, outlun, outfilename
    writeu, outlun, data_array[*,*,j]
    close, outlun
    free_lun, outlun

ENDFOR

;
;   THE OUTPUT FILES MAY BE VIEWED AS A MIP BY ANY
;   STANDARD SOFTWARE PACKAGE, e.g. "NIH View" BY
;   WAYNE RASBAND AT THE NATIONAL INSTITUES OF HEALTH
```

;

END ; AVS Arterial enhance program

What is claimed is:

1. A method for improving visualization of magnetic resonance angiography data taken from a patient, the method comprising:

providing a display device;

acquiring a first set of data representing a steady state contrast enhancement of an arterial blood pool and a venous blood pool of the patient;

acquiring a single second set of data that, in combination with the first set of data, provides information sufficient to differentiate between the arterial blood pool and the venous blood pool of the patient;

combining intensities in predetermined locations by a predetermined amount of the first and the second sets of data to produce a third set of data representing the arterial and the venous blood pools in comparable resolution with each other; and displaying the third set of data upon the display device.

2. A method according to claim 1, further comprising registering the first set and the second set of data with respect to each other.

3. A method according to claim 2, wherein registering the first set and the second set of data comprises using header information in a DICOM image.

4. A method according to claim 1, further comprising interpolating the data from one of the first and the second sets to the other of the first and the second sets.

5. A method according to claim 1, wherein acquiring a second set of data comprises acquiring a second set of data using dynamic magnetic resonance angiography acquisition.

6. A method according to claim 1, wherein acquiring a second set of data comprises acquiring a second set of data using phase contrast.

7. A method according to claim 1, wherein acquiring a second set of data comprises determining a second set of data by post processing of the first set of data using a computer.

8. A method according to claim 1, wherein combining intensities of the first and the second sets of data comprises increasing the intensity of voxels corresponding to the arterial blood pools in first set of data.

9. A method according to claim 1, wherein combining intensities of the first and the second sets of data comprises producing an output data set O according to an equation $O=\alpha S \pm \beta D_1$, wherein $\alpha$ and $\beta$ are predetermined relative weights of an intensity manipulation.

10. A method according to claim 1, wherein the first set of data is obtained at a time delayed from an introduction of a contrast agent to the patient.

11. A method according to claim 10, wherein the contrast agent is selected from the group consisting of: MS-325, MultiHance, and Magnevist.

12. A method for improving visualization of magnetic resonance angiography data taken from a patient, the method comprising:

providing a display device;

acquiring a first set of data representing a three dimensional magnetic resonance angiogram at a time delayed from an introduction of a contrast media to the patient so as to obtain information defining a steady state contrast enhancement of an arterial blood pool and a venous blood pool of the patient;

acquiring a single second set of data that, in combination with the first set of data, provides information sufficient to differentiate between the arterial blood pool and the venous blood pool of the patient;

registering the first set and the second set of data with respect to each other;

interpolating the data from one of the first and the second sets to the other of the first and the second sets;

combining a predetermined percentage of the first data set to a predetermined percentage of the second data set such that a third set of data is created representing the arterial and the venous blood pools in comparable resolution with each other; and displaying the third set of data upon the display device.

13. A method according to claim 12, wherein acquiring a second set of data comprises acquiring a second set of data using dynamic magnetic resonance angiography.

14. A method according to claim 12, wherein acquiring a second set of data comprises acquiring a second set of data using phase contrast.

15. A method according to claim 12, wherein acquiring a second set of data comprises acquiring a second set of data by post processing of the first set of data using a computer.

16. A method according to claim 12, wherein adjusting an intensity of one of the first and the second sets of data comprises increasing the intensity of voxels corresponding to the arterial blood pools in first set of data.

17. A method for improving visualization of magnetic resonance angiography data taken from a patient, the method comprising:

providing a display device;

acquiring a first set and a single second set of data, consisting essentially of:

acquiring the first set of data defining a three dimensional magnetic resonance angiogram at a time delayed from an introduction of a contrast media to the patient so as to obtain information representing a steady state contrast enhancement of an arterial blood pool and a venous blood pool of the patient; and acquiring the single second set of data representing information sufficient to differentiate between the arterial blood pool and the venous blood pool of the patient;

registering the first set and the second set of data with respect to each other;

interpolating the data from one of the first and the second sets to the other of the first and the second sets;

combining intensities in predetermined locations by a predetermined amount of the first and the second sets of data to create a third set of data representing the arterial and the venous blood pools in comparable resolution with each other; and displaying the third set of data upon the display device.

18. A method according to claim 17, wherein acquiring a second set of data comprises acquiring a second set of data using dynamic magnetic resonance angiography.

19. A method according to claim 17, wherein acquiring a second set of data comprises acquiring a second set of data using phase contrast.

20. A method according to claim 17, wherein acquiring a second set of data comprises acquiring a second set of data by post processing of the first set of data using a computer.

21. A method according to claim 17, wherein registering the first set and the second set of data comprises using header information in a DICOM image.

22. A method according to claim 17, wherein combining intensities of the first and the second sets of data comprises increasing the intensity of voxels corresponding to the arterial blood pools in first set of data.

* * * * *